(12) United States Patent  
Smith

(10) Patent No.: US 6,645,149 B1  
(45) Date of Patent: Nov. 11, 2003

(54) ULTRASOUND DEVICES

(75) Inventor: Leonard Smith, Ringwood (GB)

(73) Assignee: Deltex (Guernsey) Limited, Guernsey (GB)

( * ) Notice: Subject to any disclaimer, the term of this patent is extended or adjusted under 35 U.S.C. 154(b) by 0 days.

(21) Appl. No.: 09/958,580

(22) PCT Filed: Apr. 13, 2000

(86) PCT No.: PCT/GB00/01412  
§ 371 (c)(1),  
(2), (4) Date: Feb. 28, 2002

(87) PCT Pub. No.: WO00/61006  
PCT Pub. Date: Oct. 19, 2000

(30) Foreign Application Priority Data

Apr. 13, 1999 (GB) ............................................. 9908427

(51) Int. Cl.⁷ ................................................. A61B 8/00
(52) U.S. Cl. ...................................................... 600/459
(58) Field of Search .......................... 439/620; 606/32, 606/34, 39–41; 607/122; 600/437, 459–471

(56) References Cited

U.S. PATENT DOCUMENTS

| 5,081,993 | A | * | 1/1992 | Kitney et al. ................ 600/463 |
| 5,295,485 | A | * | 3/1994 | Shinomura et al. ......... 600/443 |
| 5,487,386 | A | * | 1/1996 | Wakabayashi et al. ...... 600/437 |
| 5,585,546 | A | * | 12/1996 | Gururaja et al. ........... 73/1 DV |
| 5,951,477 | A | * | 9/1999 | Ragauskas et al. ......... 600/438 |
| 6,308,089 | B1 | * | 10/2001 | von der Ruhr et al. ..... 600/338 |

* cited by examiner

Primary Examiner—Francis J. Jaworski  
(74) Attorney, Agent, or Firm—Welsh & Katz, Ltd.

(57) ABSTRACT

The invention provides an ultrasound probe for use in a Doppler ultrasound haemodynamic monitor having a host signal processor and an interconnect cable. The probe includes a memory device, preferable in the form of E²PROM which communicates with the host processor to limit the life of the probe and to render the probe inoperable in the event an attempt is made to use the probe in conjunction with more than one patient.

17 Claims, 3 Drawing Sheets

ULTRASOUND DEVICES

FIELD OF THE INVENTION

This invention relates to an ultrasound device and, in particular, to a disposable ultrasound probe insertable into a body cavity to enable ultrasound insonation of internal vessels and organs. Aspects of the invention may, however, be applied to other non-invasive ultrasound devices such as those which are placed in contact with the body outer surface.

BACKGROUND

Ultrasound is widely used in medicine for imaging and/or diagnostic purposes. In one form of device, ultrasound transmit and receive crystals are mounted on the tip of a probe which, in use, is located within the body so that specific organs or vessels can be subjected to ultrasound insonation and the reflected signals then analysed to give particular diagnostic information. In another form of device, the transmit and receive crystals are mounted in contact components designed to be held in contact with the body outer surface adjacent the organs or vessels to be insonated.

This company has, for some time, been manufacturing and selling an instrument for determining cardiac function. This instrument incorporates a disposable probe which is inserted into the patient's oesophagus, the probe having mounted on the outer end thereof, ultrasound transmit and receive crystals. In use, the probe is aligned so that the crystals are aligned substantially at 45° to the patient's descending aorta and are thus arranged to insonate a section of the descending aorta with ultrasound.

The probe is specifically designed and intended as a disposable device yet medical staff will, in some situations, still attempt to re-use probes on other patients. This practice carries with it a risk of cross-infection. Further, successive sterilisations intended to reduce the risk of cross-infection, can lead to a breakdown of the probe components which are not designed for such treatment.

A further characteristic of these disposable probes is that the level of ultrasound to which the patient is subjected, will vary from probe to probe. Typically this is because the receive and transmit crystals are mass manufactured from commercial grade materials and are thus susceptible to quality, and thus performance, variations.

It is therefore an object of this invention to provide an ultrasound device which will go at least some way in addressing the above-mentioned drawbacks, or which will at least provide a useful choice.

SUMMARY OF THE INVENTION

Accordingly, in one aspect, the invention provides a method of controlling the use of a disposable ultrasound device used in conjunction with a host processor to monitor physiological behaviour of a human subject, said method including the steps of:
  storing acceptable use parameters in electronic memory embodied within said disposable device;
  causing said host processor to communicate with said electronic memory; and
  controlling the ability of said host processor to function in conjunction with said disposable device in response to variations or attempted variations arising in said use parameters.

Preferably said method includes storing in said electronic memory an acceptable total time of use of said disposable device, and preventing said host further operating in conjunction with said device when said device has been in use for a time equal to said acceptable total time.

Preferably said method includes storing patient physical data within said electronic memory and preventing said host processor from communicating any variation in said patient physical data to said electronic memory. Said patient physical data may include weight, height and/or age.

Preferably said method includes causing a host processor to record a date of first use of said device in said electronic memory, and causing a host processor to no longer function with said device at a predetermined time after said date of first use.

Preferably the date of manufacture of said device is recorded in said electronic memory, said method including causing a host processor to no longer function in conjunction with said device after the passage of a predetermined period of time after said date of manufacture.

In a second aspect the invention provides an ultrasound device for use in conjunction with a host processor to monitor physiological behaviour of a human subject, said device including electronic memory able to communicate with said host processor when said device is in use, said electronic memory being constructed and arranged to store patient use data parameters.

Preferably said electronic memory is operable to store information relating to the accumulated time of use of said device. More preferably said electronic memory contains a counter of remaining time available for use, said counter declining whilst said device is in use until zero is reached after which said device will no longer function in conjunction with a host processor.

Preferably said electronic memory contains a plurality of time counters, said host processor maintaining a host counter internally initiated from that one of said time counters in electronic memory indicating the lowest remaking time of use, said host processor updating the permissible remaining time of use alternatively between said time counters in memory.

Preferably said electronic memory is further operable to store patient physical details such as weight, height and/or age.

Preferably said device comprises a probe insertable into a body cavity.

Preferably said probe includes a connector for connection thereof to said system processor, said electronic memory means being included in said connector.

Preferably said electronic memory means comprises an E$^2$PROM.

Said probe may include one or more further transducer[s]operable to monitor predetermined patient parameters. Such parameters may, for example, comprise temperature or pulse oxygen levels.

In a third aspect the invention provides a Doppler ultrasound cardiac function monitor including an probe as hereinabove set forth locatable in the oesophagus of a human; and a host processor connectable to said probe, said host processor being constructed and arranged to communicate with said electronic memory and to render said monitor inoperable in response to predetermined variations or attempted variations arising, in real time, to one or more parameters stored in said electronic memory.

In a fourth aspect the invention provides an ultrasound device for insonating part of a human subject, said device including ultrasound transmit and receive means as well as at least one other transducer operable to monitor a physiological parameter of a human subject.

Preferably said transducer is operable to monitor said physiological parameter during operation of said ultrasound transmit and receive means.

In a fifth aspect the invention provides a method of calibrating an ultrasound transmit and receive device used in conjunction with a human subject, said method including the steps of associating electronic memory means with said device; subjecting said device to a signal of known characteristics; and storing the response of said device to said signal in said electronic memory.

Many variations in the way the present invention can be performed will present themselves to those skilled in the art. The description which follows is intended as an illustration only of one means of performing the invention and the lack of description of variants should not be regarded as limiting. Wherever possible, a description of a specific element should be deemed to include equivalents thereof whether in existence now or in the future. The scope of the invention should be limited by the appended claims alone.

BRIEF DESCRIPTION OF THE DRAWINGS

One form of the invention will now be described with reference to the accompanying drawings in which.

DETAILED DESCRIPTION OF WORKING EMBODIMENT

Figure 1:
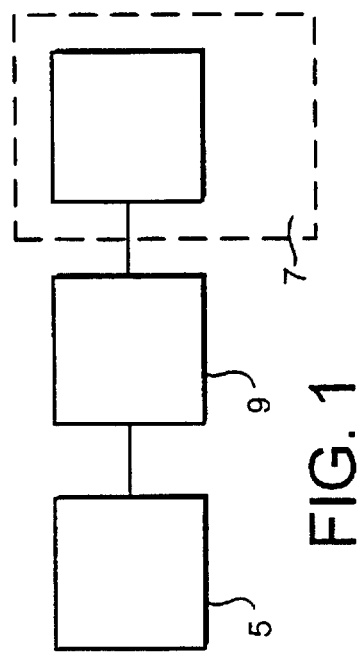
FIG. 1: shows a schematic system outline of a Doppler ultrasound cardiac output monitor incorporating an ultrasound probe according to the invention.

Referring to the drawings, the present invention provides a disposable ultrasound transmit and receive device for use in conjunction with a host processor to provide diagnostic and/or imaging data derived from a human subject. Whilst such a device could be adapted for contacting the body outer surface, the following description is directed to a probe 5 insertable into a human body cavity [not shown].

The particular form of probe herein depicted and described comprises a disposable oesophageal probe for use in a Doppler ultrasound cardiac function monitor. In this application, the probe is connected to a host system processor 7 which causes the probe 5, when located in a patient's oesophagus, to emit ultrasound in the direction of the descending aorta, and to receive signals reflected off red blood cells moving through the aorta. The ultrasound signals are then processed to give a measure of blood velocity. Details of patient weight, height and age are also processed within the host system processor, according to an accepted statistically based method, to give a measure of aorta cross section, the resulting measure of cross section then being combined with blood velocity to give an indication of cardiac function.

In the form of apparatus shown in FIG. 1, the probe 5 is connected to the host system processor 7 through a patient interconnect cable [PIC] 9, all the components having electronic components which will be described, at least in part, below.

In the conventional manner, the probe 5 comprises a flexible elongate shaft member 11, at the free end of which ultrasound receive and transmit crystals [not shown] are mounted, the ultrasound crystals being covered by a soft plastics or rubber boot 13. The opposite end of the shaft 11 carries a connector 15 whereby the probe may be connected into the host system processor 7, in this case via the PIC 9.

In accordance with this invention, the probe 5 has embodied therein, an electronic memory which can receive and store probe/patient use parameters. Some parameters may be entered into memory in manufacture whilst others will be inserted when the probe is connected to the host system processor 7.

In use, the host processor communicates with the memory in the probe in relation to one or more of the parameters which are stored in memory. In the case of some parameters, the host processor will render the monitor inoperative if the parameter monitored in real time varies from its stored value in a predetermined way. By way of example, a maximum permissible time of use may be recorded in the memory embedded in the probe. When the actual time of use equates to the total period of permissible use, the host system processor recognises the fact and the monitor will no longer function with that probe attached.

In the case of other parameters, the host system processor 7 may simply decline to allow a variation in the parameter to be accepted with that particular probe connected. For example, when initial patient use data such as age, weight and height have been entered in the memory embedded in the probe, the host system processor will recognise that this data has been recorded and will not allow any variation thereto.

Figure 2:
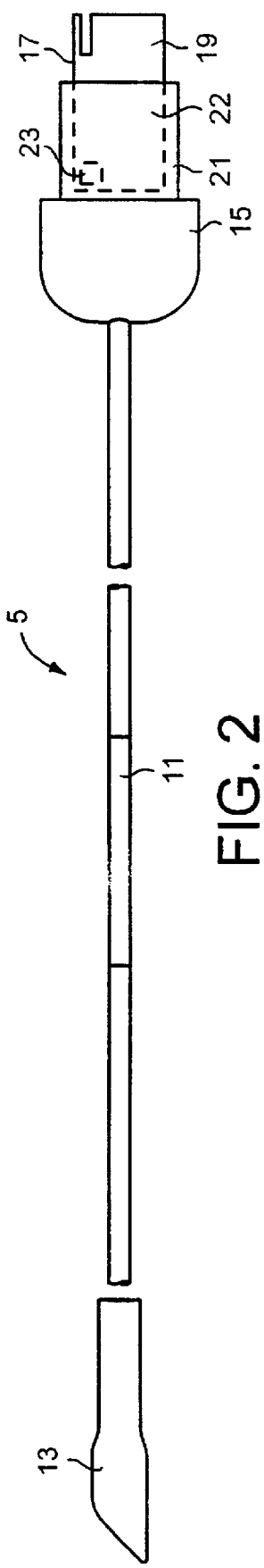
FIG. 2: shows a plan view of an ultrasound probe according to the invention.
Figure 3:
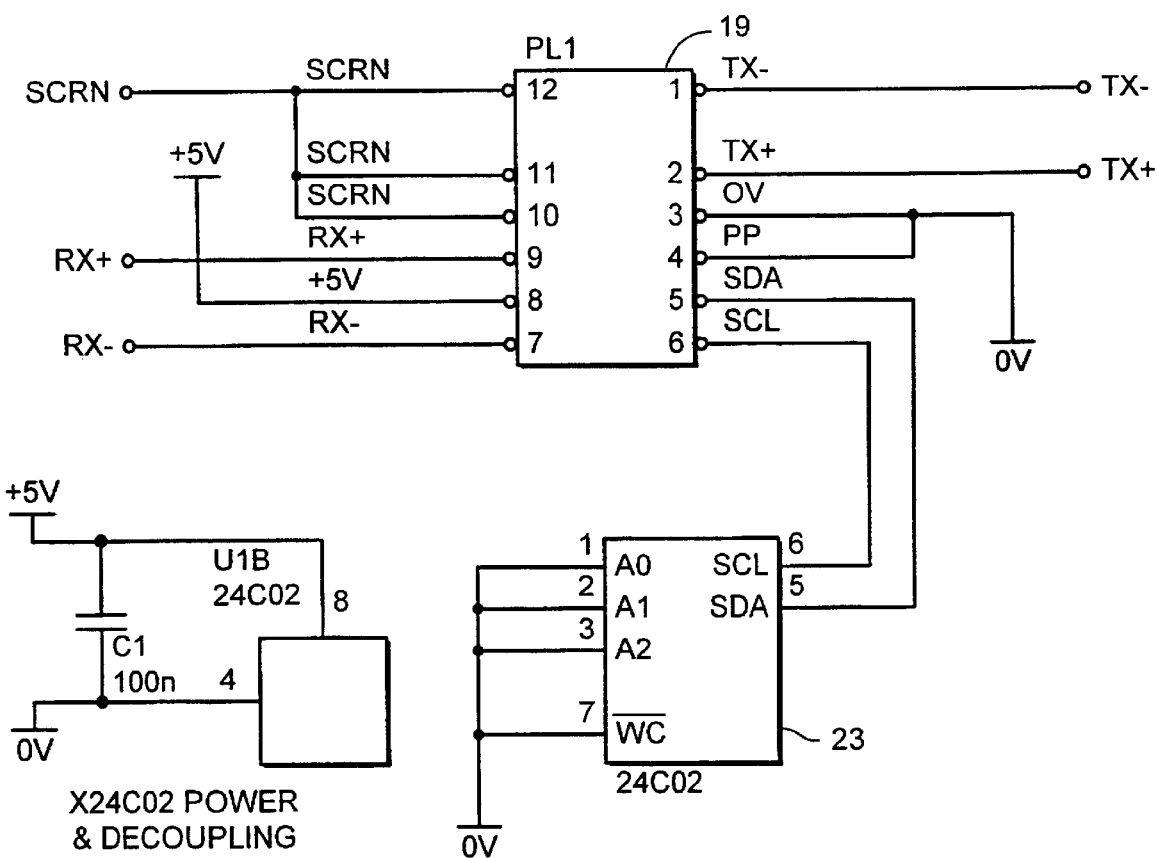
FIG. 3: shows a schematic outline of the electronic components included in the probe shown in FIG. 2.

In the form shown in FIGS. 2 and 3, the electronic memory is embodied in the connection 15 between the probe 5 and the PIC 9. More particularly the connection 15 is preferably defined, in part, by a printed circuit board 17, edge part 19 of which projects to form a connection with the PIC 9, and part 21 of which is enveloped in an insulating cover 22. The electronic memory, preferably in the form of an $E^2PROM$ 23, is mounted on the printed circuit board 17.

Whilst the memory is preferably in the form of an $E^2PROM$ and is described herein as such, it will be appreciated by those skilled in the art, that the memory could take other forms, eg a flash ROM.

The PIC 9 obviously provides an electrical connection with the host system processor 7 and may include preamplification means to amplify the receive signals from the probe before transmission to the host system processor 7.

In use, when a new probe 5 is connected to host system processor 7, the date of first use, as advised by the system processor, is immediately recorded in $E^2PROM$ 23. The host processor also interrogates the timer locations in memory and, if the probe is new and these locations are empty, the host processor allocates a maximum allow time of use to these memory locations. Alternatively, as part of the manufacturing process, the memory 23 could be programmed with a total time of permissible use.

Thereafter, a counter in the processor 7 continually measures the time of use and periodically updates the $E^2PROM$ 23 by subtracting the elapsed time of use from the total permissible time of use remaining in memory 23. When permissible time stored in $E^2PROM$ 23 reaches zero, the host system processor 7 is triggered and thereafter declines to operate with that particular probe connected.

To guard against the possibility of power failure or cut-off while the host processor is updating the time counter in memory 23, memory 23 preferably includes two locations or counters which are updated alternately by the host processor 7. Thus, the host processor reads both counter locations and updates the higher reading. In normal operation, the internal counter in the system processor 7 updates the probe counters every hour however, when the internal counter in the host processor 7 reaches zero, the host immediately writes both counters in E $^2$PROM 23 to zero. Thereafter, as soon as the monitor is switched off, or the probe 5 is disconnected, the probe 5 will no longer operate with a host processor 7. The host system processor is also programmed to render the probe inoperable after a predetermined time has elapsed after the date of first use [say four days], regardless of whether or not time remains in the time counters forming part of E $^2$PROM 23.

During manufacture, the E $^2$PROM 23 is preferably also programmed with date of manufacture, thus allowing a "shelf-life" to be built into the probe. Upon connection, the host system processor will interrogate the date of manufacture and if the connection date exceeds the date of manufacture by a predetermined length of time, the host processor 7 will decline to function with that probe connected.

As stated above, the probe 5 as described herein, is designed to form part of a cardiac function monitor which uses a statistically based method, based on patient age, weight and height, to determine typical aortic cross sectional area. Thus, the memory 23 in the probe 5 is configured to receive details of age, weight and height of a particular patient into whom the probe is to be inserted.

Upon initial connection, the host system processor 7 interrogates E $^2$PROM 23 to determine if patient age weight and height have been recorded. If not, the host processor 7 calls for the monitor operator to enter and confirm these details. Once entered and confirmed, a host processor connected to the probe 5 will not allow these details to be amended.

Figure 4:
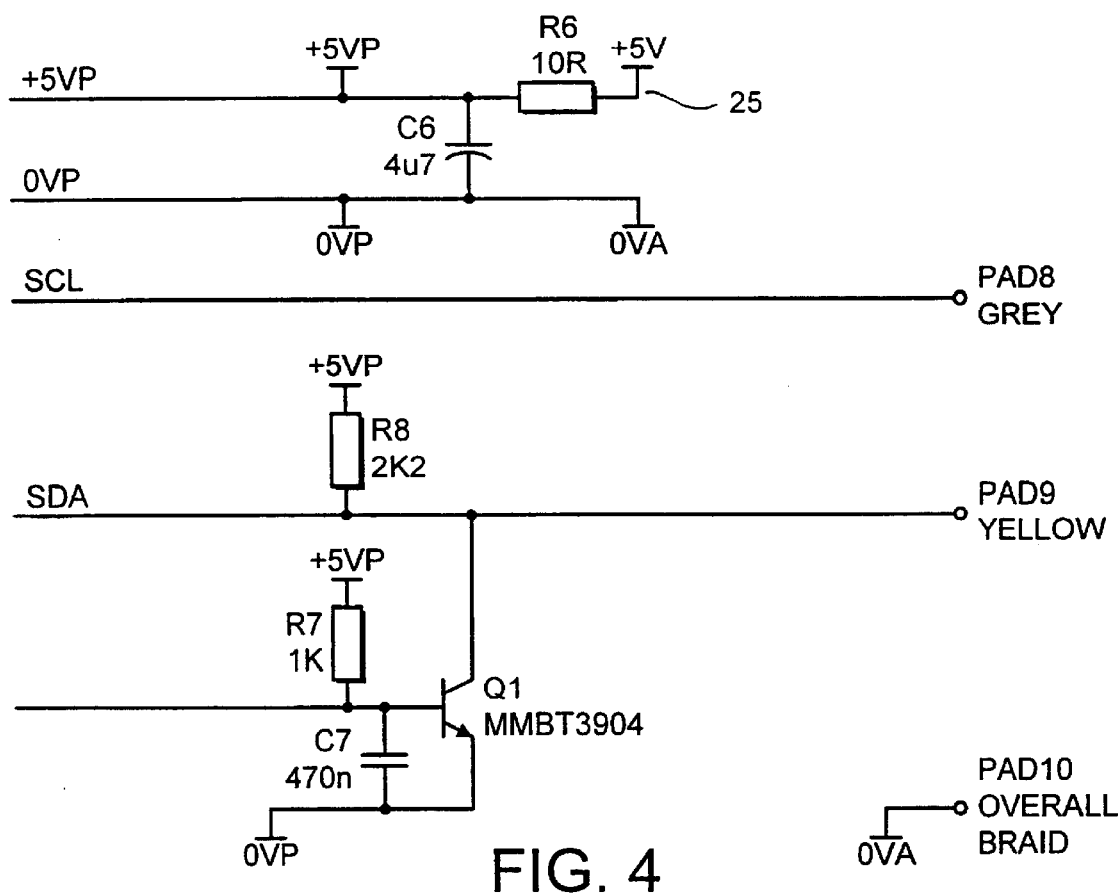
FIG. 4: shows a schematic outline of certain electronic components incorporated in a patient interconnect cable and arranged to operate in conjunction with the components shown in FIG. 3.

Turning now to FIGS. 3 and 4, the probe 5, PIC 9 and system processor 7 incorporate an industry standard communications bus, in this case a Philips I $^2$C bus, to allow data to be passed therebetween. To this end, connector edge part 19 on the probe connector 15 includes pins SDA and SCL for the serial data and serial clock lines respectively. These engage with the corresponding SDA and SCL pins on the PIC 9 and lead back to the host system processor, to enable communication between the host system processor 7 and the E $^2$PROM 23. Power and decoupling device C1 is provided to power and decouple the E $^2$PROM 23.

Pin PP on the probe contacts corresponding PP on the PIC 9 [FIG. 4], the PP connection on the PIC 9 serving not only to indicate when a probe is connected to the PIC 9 but also, to release the SDA line for the passage of data between the processor 7 and the probe 5. More particularly, and with reference to FIG. 4, when there is no probe present, Q1, R7 and C7 hold the SDA line low at just over 0 volts. When a probe is present, PP on the PIC 9 is held low (connected to ground) and Q1, R7 and C7 release the SDA line to pass data. Thus the SDA line provides the dual function of passing data and indicating the connection, or not, of a probe.

PIC 9 receives power at 5 volts from the host processor 7 and uses this power to power E $^2$PROM 23, but includes components R6,C6 [25] to filter out noise induced in the PIC cable.

The use of a disposable probe 5 with a PIC 9 having the amplification facilities mentioned, allows extra capability to be built into the probe. For example, the probe could be provided with one or more additional transducers [not shown] to allow patient physiological parameters such as, for example, temperature or pulse oxygen to be monitored—preferably simultaneously with cardiac function.

There are further advantages in including a memory device in the probe. For example, the device can store calibration information relating to the probe which will increase the likelihood of the patient being subjected to uniform levels of insonation. Due to variations arising in the high volume manufacture of the crystal materials used for the ultrasound transmit and receive components, performance variations are inevitable from one probe to another and this could lead to patients being subjected to varying levels of power.

With a view to ensuring patients are subjected to substantially known and constant levels of power, the desired output characteristics of the probe can be written into the E $^2$PROM 23 during manufacture and, at the end of the production process, a signal of known characteristics applied to the probe and the resulting probe response also stored in the E $^2$PROM to give a calibration factor. The system processor 7 can be programmed to apply this calibration factor during use of the probe to ensure a consistent transmit power output.

In use, whether calibrated or not, a probe 5 is connected to PIC 9 and to host system processor 7. Assuming the probe has not previously been used, the system processor 7 will note that the clock counters contain the full permitted time of use and will also note that the patient data register is empty. The monitor, under the control of host system processor 7, will then call for patient age, weight and height to be entered and confirmed and, upon the data being so entered and confirmed, will pass this to memory 23. As the probe is used, the clock register in E $^2$PROM 23 is continuously counted-down until the permitted use time reaches zero. Thereafter the processor 7 will not allow the monitor to function with that particular probe in place. In a similar manner, the system processor communicates with the patient physical data first entered in memory 23 and will not allow any variation thereof.

It will thus be appreciated that the present invention, at least in respect of the preferred form of apparatus described herein, provides a form of ultrasound probe which remains inexpensive to manufacture but which guards against re-use.

What is claimed is:

1. An ultrasound probe for use in conjunction with a host processor to monitor physiological behaviour of a human subject, said probe including an electronic memory able to communicate with said host processor when said probe is in use, said electronic memory being configured and operable to store information relating to the accumulated time of use of said probe together with one or more patient physical details selected from the group consisting of weight, height and age.

2. A probe as claimed in claim 1 wherein said electronic memory contains a counter of remaining time available for use, said counter declining while said device is in use.

3. A probe as claimed in claim 2 wherein said device includes a plurality of counters, said host processor maintaining a host counter initiated from that one of said time counters in electronic memory indicating the lowest remaining time of use, said host processor updating the permissible time of use alternatively between said counters in memory.

4. A probe as claimed in claim 1 comprising a probe insertable into a body cavity.

5. A probe as claimed in claim 1 including a connector for connection thereof to said host processor, said electronic memory being included in said connector.

6. A probe as claimed in claim 1 is wherein said electronic memory comprises an $E^2PROM$.

7. A probe as claimed in claim 6 further including one or more transducers operable to monitor predetermined patient parameters.

8. A probe as claimed in claim 1 further including one or more transducers operable to monitor predetermined patient parameters.

9. A probe as claimed in claim 8 wherein said patient parameters comprise temperature or pulse oxygen levels.

10. A Doppler ultrasound cardiac function monitor including a probe as claimed in claim 1 locatable in the oesophagus of a human; and a host processor connectable to said probe, said host processor being constructed and arranged to communicate with said electronic memory and to render said monitor inoperable in response to predetermined variations occurring in the data stored in said electronic memory.

11. An ultrasound probe for use in conjunction with a host processor to monitor physiological behaviour of a human subject, said probe including an electronic memory capable of communicating with said host processor when said probe is in use, said electronic memory including a plurality of time counters capable of communicating with a host counter in said host processor one of said time counters in said electronic memory indicating the lowest remaining time of use, said one of said time counters initiating the communication of said host counter with said plurality of time counters, the permissible time of use of said plurality of time counters being updated from said host processor alternatively between said plurality of time counters.

12. A probe as claimed in claim 11 wherein said electronic memory is further operable to store patient physical details selected from a group comprising weight, height and age.

13. A probe as claimed in claim 11 comprising a probe insertable into a body cavity.

14. A probe as claimed in claim 11 including a connector for connection thereof to said host processor, said electronic memory being included in said connector.

15. A probe as claimed in claim 11 is wherein said electronic memory comprises an $E^2PROM$.

16. A probe as claimed in claim 11 further including one or more transducers operable to monitor predetermined patient parameters.

17. A Doppler ultrasound cardiac function monitor including a probe as claimed in claim 11 locatable in the oesophagus of a human; and a host processor connectable to said probe, said host processor being constructed and arranged to communicate with said electronic memory and to render said monitor inoperable in response to predetermined variations occurring in the data stored in said electronic memory.

* * * * *